United States Patent [19]

de Vleesschauwer et al.

[11] 4,153,637

[45] May 8, 1979

[54] USE OF AMMONIA IN THE FORMATION OF AROMATIC HYDROCARBONS BY DEHYDROISOMERIZING ALKYLCYCLOPENTANE WITH A PLATINUM HYDROGEN MORDENITE CATALYST

[75] Inventors: Walter F. de Vleesschauwer, Ghent; Alan Molyneux, Mariakerke, both of Belgium

[73] Assignee: s.a. Texaco Belgium n.v., Brussels, Belgium

[21] Appl. No.: 863,981

[22] Filed: Dec. 23, 1977

[30] Foreign Application Priority Data

Feb. 22, 1977 [GB] United Kingdom .................. 7294/77

[51] Int. Cl.² .......................... C07C 5/24; C07C 5/26; C07C 5/32
[52] U.S. Cl. ..................................... 585/405; 585/374; 208/46; 208/130
[58] Field of Search ............ 260/683.2, 668 A, 668 D, 260/666 A

[56] References Cited

U.S. PATENT DOCUMENTS

| | | |
|---|---|---|
| 2,849,377 | 8/1958 | Ogburn et al. ..................... 260/683.5 |
| 3,630,961 | 12/1971 | Wilhelm ............................. 260/683.2 |
| 3,632,525 | 1/1972 | Rausch ............................... 260/683.2 |
| 3,751,502 | 8/1973 | Hayes et al. ...................... 260/683.2 |
| 3,772,400 | 11/1973 | Garner et al. ..................... 260/683.2 |
| 3,997,618 | 12/1976 | Cornely et al. .................. 260/668 A |

Primary Examiner—Veronica O'Keefe
Attorney, Agent, or Firm—Thomas H. Whaley; Carl G. Seutter; George J. Darsa

[57] ABSTRACT

A process for the dehydroisomerization of hydrocarbons in the presence of a catalyst composed of a metal of Group VIII supported on mordenite in hydrogen form and treated with ammonia.

13 Claims, 2 Drawing Figures

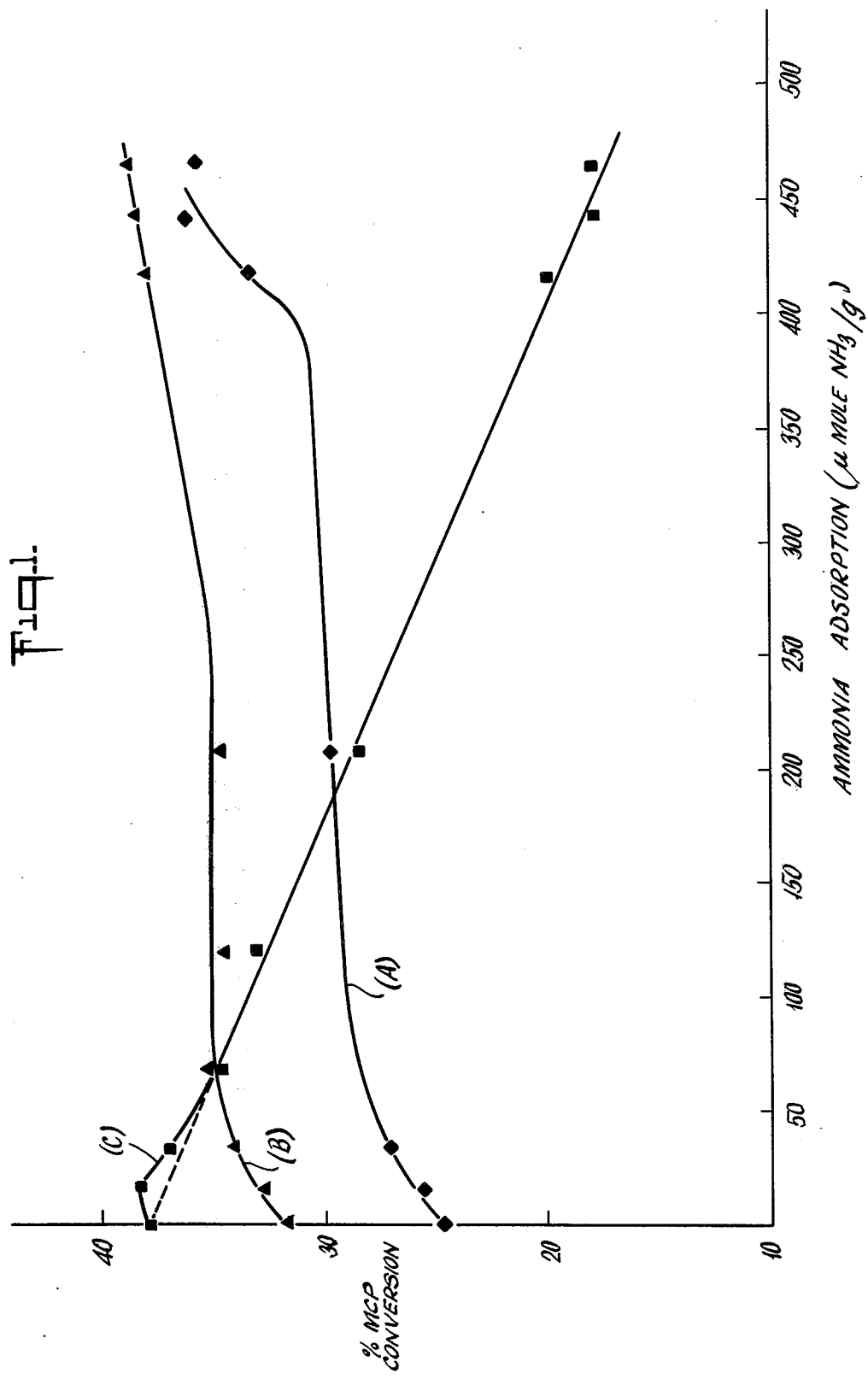

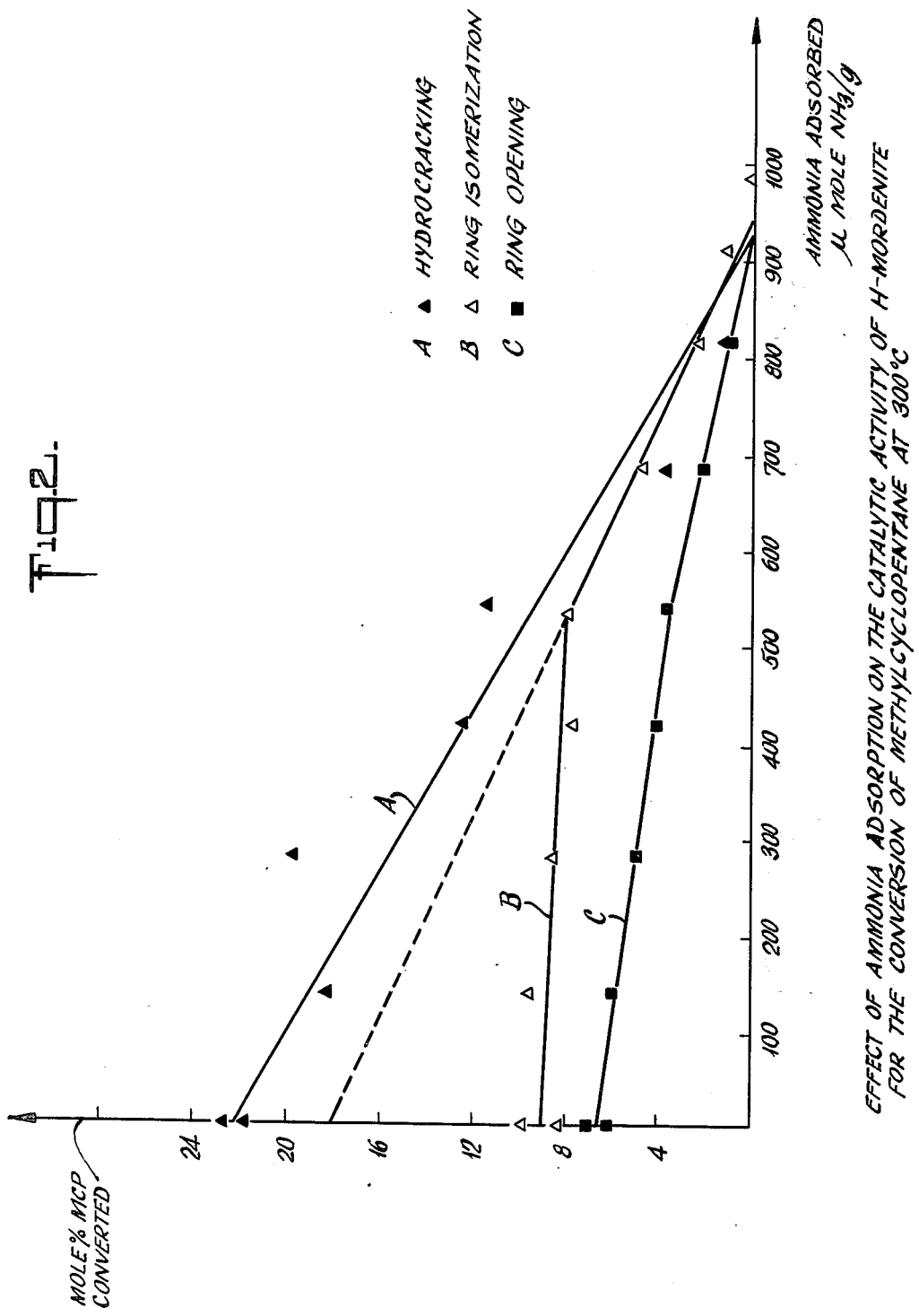

USE OF AMMONIA IN THE FORMATION OF AROMATIC HYDROCARBONS BY DEHYDROISOMERIZING ALKYLCYCLOPENTANE WITH A PLATINUM HYDROGEN MORDENITE CATALYST

BACKGROUND OF THE INVENTION

This invention concerns the dehydroisomerization of hydrocarbons. These hydrocarbons may be aliphatic in nature, but the process of this invention is especially suitable for the dehydroisomerization of alkylcyclopentanes, and of hydrocarbon feedstocks containing alkylcyclopentanes, into aromatic hydrocarbons. In a preferred embodiment, it concerns the dehydroisomerization of methylcyclopentanes into benzene and toluene in the presence of a specific catalyst system.

Alkylcyclopentanes are found as components of light straight run gasoline, and are contained in other gasoline fractions, such as naphtha fractions resulting from thermal and catalytic conversion of petroleum. Typically, saturated gasoline or naphtha fractions are treated or upgraded to improve their anti-knock characteristics. One means of upgrading such streams is by the well known process of reforming, wherein naphthenic hydrocarbons such as cyclohexane compounds are dehydrogenated to aromatics. Subjecting five membered naphthene ring compounds such as alkylcyclopentanes to conventional dehydrogenation or reforming catalysts and processing conditions, however, causes the formation of minor amounts of cyclic mono-olefins and di-olefins in addition to the production of undesirable amounts of carbonaceous deposits on the catalyst in view of the susceptibility of naphthenes to cracking. While some isomerization of alkylcyclopentanes to cyclohexanes may occur, the overall effect has been to downgrade such cmponents to less valuable products having little or no value as gasoline blending components. Likewise, the practice of separating five membered naphthene ring hydrocarbons for separate isomerization of such compounds to cyclohexanes followed by dehydrogenation of the cyclohexanes to aromatics, is at best a poorly selective process involving the use of a plurality of catalysts and reaction zones, which is economicaly unattractive from a processing standpoint.

It is known that hydrogen mordenite is a suitable substrate for catalytically active metals, and has been used in a variety of hydrocarbon isomerization and conversion processes. See, for instance, U.S. Pat. Nos. 3,432,568; 3,475,345; 3,507,931; 3,574,092; 3,409,685 and 3,709,817; and a paper by Minachev et al. in Izv. Akad. Nauk SSSR, Ser. Khim. 8, 1737–42 (August 1969). It is, however, a problem that hydrogen mordenite itself exhibits considerable cracking activity, leading to undesirably low yields of isomerized product, and wastage of feedstocks.

Attempts have been made in the past to suppress the cracking activity of a catalyst by the use of a catalyst poison. For example, British Pat. No. 1.009,943 shows that the course of reactions carried out on zeolitic aluminosilicate catalysts can be controlled by the use of appropriate catalyst poisons. For instance, dehydration, hydration, cracking and olefin isomerization processes are all acid-catalyzed and suppressed by basic catalyst poisons; while hydrogention is catalyzed by transition metals and poisoned by sulphur, nitrogen and phosphorus compounds.

British Pat. No. 1,266,781 describes a process wherein the cracking activity of the outer surface of a porous zeolitic molecular sieve catalyst is decreased by poisoning with ammonia, an alkylamine or carbon disulphide at a temperature from 400 to 1000° F., while the activity of the inner surface of the pores is not substantially decreased. As a result, liner hydrocarbons, such as n-hexane, can still be cracked, while the more bulky branched hydrocarbons, such as 3-methylpentane, cannot enter the pores and are not cracked.

An object of this invention is to provide a process for the hydroisomerization of hydrocarbons, and especially the dehydroisomerization of alkylcyclopentanes into aromatic products, in which cracking of the feedstock is minimized.

It has now surprisingly been found that, by working under carefully controlled temperature conditions, not only is the cracking activity of a hydrogen mordenite catalyst suppressed by contacting the catalyst with ammonia, but the isomerization reaction, which is also known to be acid-catalyzed, and hence poisoned by bases, is maintained. It is thereby possible to provide a hydrocarbon dehydroisomerization process of enhanced selectivity.

DESCRIPTION OF THE INVENTION

The present invention provides a process for the dehydroisomerization of hydrocarbons, which comprises contacting a hydrocarbon charge stock at an elevated temperature of at least 330° C., and in the presence of hydrogen with a catalyst comprising a metal of Group VIII of the Periodic System supported on mordenite in hydrogen form and treated with ammonia.

The catalyst used in the process of the invention comprises a Group VIII metal on a hydrogen mordenite. Any metal of Group VIII can be employed, for instance rhodium, palladium, iridium, platinum, or ruthenium. The preferred Group VIII metal is, however, platinum. The amount of the Group VIII metal is not critical, but the catalyst can coveniently comprise from about 0.01 to 5.0 weight percent, most preferably from about 0.1 to 1.0 weight percent of a Group VIII metal such as platinum.

The Group VIII metal can also be employed in conjunction with a metal of Group VI A or VII A of the Periodic Table. The form of Periodic Table referred to is that shown on page 183 of "General and Inorganic Chemistry" by Partington; (MacMillan & Co., London) Second Edition (1951). A suitable Group VII A metal is rhenium which may, for example be used in an amount from 0.01 to 1.0 weight percent based on catalyst.

Hydrogen mordenite is a well known catalyst substrate, as shown for instance by the documents referred to above. It can, for instance, have a silica : alumina mole ratio from 10:1 to 100:1. It can be made, for example, by ion-exchanging a natural or synthetic mordenite with an acid, or, more preferably, by ion-exchanging the mordenite with ammonia and decomposing the resulting ammonium mordenite by heating. A convenient method for preparing the catalyst used in this invention is by impregnating hydrogen mordenite with tetramine platinum (II) chloride monohydrate [Pt(NH$_3$)$_4$]Cl$_2$, H$_2$O. The preparation of the Pt complex is described in "Inorganic Synthesis" Vol. II, p. 250. Ed. W. G. Fernelius.

The dehydroisomerization reaction is carried out at elevated temperature of above 330° C. A convenient temperature for this reaction is in the range of from 350° to 500° C., most preferably in the range from 350° to 400° C. The pressure employed is not critical, and atmospheric pressure, or pressures slightly above atmospheric pressure, e.g. from 5 to 500 p.s.i.a., preferably 15 to 250 p.s.i.a., can conveniently be employed. The process can be carried out either continuously or batchwise.

By virtue of the preferred embodiment of the process according to the invention, alkylcyclopentanes are converted in good yields and with good selectively into aromatic hydrocarbons. For example, a high yield of aromatics including benzene and toluene is obtained from methylcyclopentane. The process is particularly suitable, however, for the reforming of naphtha and other gasoline fractions.

In accordance with the process of the invention, the selectivity of the catalyst and the proportion of aromatic hydrocarbons in the product are enhanced by contacting the catalyst with ammonia. It is believed that under the conditions of the invention, the effect of the ammonia is to suppress the inherent cracking activity of the hydrogen mordenite. The catalyst can be subjected to the treatment with ammonia either before use in the dehydroisomerization reaction or during this reaction, either by injecting slugs of ammonia into the reaction apparatus at intervals or by injecting a continuous stream of ammonia into the apparatus. It is found that the percentage of methylcyclopentane cracked into compounds containing five carbon atoms or less exhibits a substantially linear decrease as the proportion of ammonia adsorbed by the catalyst increases. At the same time, the proportion of methylcyclopentane converted into benzene and toluene increases.

The conditions under which contact between the catalyst and the ammonia is most advantageously brought about depend inter alia upon the nature of the catalyst and the time at which the catalyst is contacted with ammonia. For instance, when the catalyst is contacted with ammonia during the dehydroisomerization reaction, the ammonia must of necessity be at the same temperature as the hydrocarbon charge stock. Temperatures in the above-mentioned range of from at least 330° C., e.g. from 350 to 500° C., most preferably from 350° to 400° C., can be used without disadvantage. In the embodiment in which contact with ammonia precedes contact with the hydrocarbon charge stock, it is better to use temperatures which are lower rather than higher. It was found, for instance, that a higher proportion of ammonia was absorbed at 350° C., than at 500° C., and gave a catalyst of greater selectivity, whereas subsequent heating at 500° C., of a catalyst that had been treated with ammonia at 350° C., resulted in partial desorption of the ammonia and a reduction in the selectivity of the catalyst to a value which was still, however, above that of an untreated catalyst.

The amount of ammonia which is employed will vary in dependence upon the number of active sites on the catalyst, which is in turn governed by the chemical composition of the catalyst. Amounts from 5 to 5000 ppm, preferably 10 to 1000 ppm can, for instance, be employed.

The conversion process according to the invention can be carried out at a L.H.S.V. of from 0.5 to 20.0, preferably from 1 to 10, V/V/H. and at hydrogen flow rates of 1000 to 10,000 SCFB, preferably from 2000 to 6000 SCFB.

The invention will be further explained by reference to the following non-limiting Examples, in which Examples 1 to 3 are provided for comparison, Examples 4 to 6 are Examples showing the process according to the invention. Example 7 is outside the scope of the invention, but is provided to explain the lower temperature limit of the invention. Example 8 shows the dehydroisomerization of n-hexane in accordance with the invention.

EXAMPLE 1

0.0541 g of tetramine platinum (II) chloride monohydrate was dissolved in a small amount of deionized, distilled water at room temperature, and the solution was diluted to approximately 100 ml. To this solution, 5.005 g of commercially available H-mordenite powder, having a silica : alumina ratio of 11.31:1 was added, and the water was slowly evaporated on the stream bath while the mixture was constantly agitated. After evaporation, the resulting catalyst was dried in air overnight at 110° C. The finished catalyst had a platinum content of 0.599 weight percent.

The catalyst (100 mg) was then placed in a pulse microreactor and was activated by heating overnight (16 h) at 200° C., in a hydrogen flow of 40 ml/min at atmospheric pressure. Then the flow rate was increased to 400 ml/min, and the catalyst was submitted to the following heat treatment.

300° C. for 30 min.
400° C. for 30 min.
500° C. for 60 min.

The temperature was then lowered to 350° C., and the flow rate of hydrogen was adjusted to 40 ml/min. The total pressure in the reactor was now 20 p.s.i.g. Successive pulse of 3 μl. of methylcyclopentane (MCP) were passed over the catalyst. Under these conditions about 36% of the MCP was converted into benzene at an overall MCP conversion of 87%. A conventional Pt/Al$_2$O$_3$ catalyst, comprising 0.6 weight percent of platinum, did not yield any benzene at a comparable temperature of 345° C., and under otherwise similar conditions.

Typical results in mole % for MCP obtained with the Pt-mordenite catalyst (Pt-HM and the Pt/Al$_2$O$_3$ catalyst are listed in Table 1.

Table 1

|  | Pt-HM | Pt/Al$_2$O$_3$ |
|---|---|---|
| C$_5$ and lower hydrocarbons | 42.5% | 0.8% |
| C$_6$ saturates | 9.0% | 18.0% |
| Aromatics | 37.6% | 0.0% |
| Total conversion | 89.1% | 18.8% |

The amount of MCP converted into C$_5$ and lower hydrocarbons (C$_5^-$) with the Pt-HM catalyst was: for CH$_4$ 0.2%; for C$_2$ 2.2%; for C$_3$ 15.4% for iC$_4$ 11.0%; for n-C$_4$ 7.7%; for iC$_5$ 4.2% and for n-C$_5$ 1.8%. Thus only about 2.4% was converted into CH$_4$ and C$_2$H$_6$. The 9.0% C$_6$ saturates consisted of 2,2-dimethylbutane (0.3%), 2-methylpentane (4.2%), 3-methylpentane (1.8%), hexane (2.0%) and cyclohexane (0.7%). Successive pulses of MCP did not cause a decline of catalyst activity.

EXAMPLE 2

A series of tests was carried out in a microreactor as described in Example 1. The catalyst comprises 100.2 mg of the platinum/hydrogen-mordenit catalyst used in Example 1, and pulses of 3 μl of MCP (Runs 1 to 5) and of hexane for comparison (Run 6) were passed over the catalyst at temperature from 350° C. to 500° C. The results obtained are set out in Table 2.

Table 2

| Run | 1 | 2 | 3 | 4 | 5 | 6 |
|---|---|---|---|---|---|---|
| Charge | MCP | MCP | MCP | MCP | MCP | hexane |
| Temperature (°C.) | 350 | 350 | 400 | 450 | 499.5 | 500 |
| $C_5$ and lower | 36.5 | 36.4 | 51.0 | 64.1 | 72.2 | 89.8 |
| $C_6$ paraffins | 8.2 | 8.3 | 2.6 | 0.2 | 0.0 | 0.0 |
| $C_6$ unsaturates | 0.0 | 0.0 | 0.4 | 0.0 | 0.0 | 0.0 |
| Naphthenes | 1.4 | 1.6 | 0.1 | 0.0 | 0.0 | 0.0 |
| Aromatics | 34.4 | 33.9 | 43.1 | 31.7 | 25.9 | 10.2 |
| Total conversion | 80.6 | 80.2 | 97.2 | 96.0 | 98.1 | 100.0 |
| Selectivity | 54.7 | 54.6 | 47.5 | 33.3 | 26.4 | 10.2 |

In the above Table 2, the figures for $C_5$ and lower, $C_6$ paraffins, $C_6$ unsaturates, naphthenes and aromatics are the molar percentage of the charge converted into each group of products. Selectivity is the ratio of charge converted into products having 6 or more carbon atoms to the overall conversion of the charge. It will be seen that the selectivity decreases with increasing temperature, because of the increased cracking activity of the catalyst at higher temperatures. The optimum temperature was from 350 to 400° C.

The aromatics content of Runs 1 to 6 was made up of benzene and toluene. The amounts of benzene, toluene and total aromatics (expressed as the molar percentage of charged converted, as in Table 2) are set out in Table 3, from which it can be seen that with MCP with toluene content of the aromatics product increases to a maximum at 400° C. and then drops again.

Table 3

| Run | 1 | 2 | 3 | 4 | 5 | 6 |
|---|---|---|---|---|---|---|
| Benzene | 25.0 | 26.0 | 23.2 | 19.7 | 17.7 | 8.4 |
| Toluene | 9.4 | 7.9 | 19.9 | 12.7 | 8.2 | 1.8 |
| Aromatics | 34.4 | 33.9 | 43.1 | 31.7 | 25.9 | 10.2 |
| Toluene content of the aromatics (%) | 27.4 | 23.4 | 46.2 | 40.2 | 31.7 | 17.6 |

EXAMPLE 3

The activity for reforming MCP of the platinum/hydrogen mordenite catalyst used in Example 1, was compared with the activity of three conventional catalysts, (A, B, and C). Contacting of the MCP with the four catalysts was carried out under the same conditions at temperatures of 350° C. and 400° C. The results are set out in Tables 4 and 5 below, from which it may be seen that the platinum/hydrogen-mordenite catalyst is both more active in bringing about isomerization, and more selective in the formation of aromatics, particularly at the lower temperature of 350° C. as shown in Table 4.

The compositions of catalysts A, B and C are as follows:
Catalyst A: 0.375 wt. % Pt. 0.2 wt. % Re on a γ-alumina base
Catalyst B: 0.375 wt. % Pt. 0.5 wt. % Re on a γ-alumina base
Catalyst C: 0.6 wt. % Pt. on a γ-alumina base Table 4

| Catalyst | Pt/H-mordenite | A | B | C |
|---|---|---|---|---|
| $C_5$ and lower | 36.5 | 0.2 | 0.0 | 1.9 |
| $C_6$ paraffins | 8.7 | 2.7 | 0.2 | 9.0 |
| $C_6$ unsaturates | 0.0 | 0.2 | 0.2 | 0.0 |
| Naphthenes | 1.4 | 0.2 | 0.2 | 0.0 |
| Aromatics | 34.5 | 1.1 | 0.6 | 1.2 |
| Total conversion | 80.6 | 4.2 | 1.1 | 22.1 |

Table 5

| Catalyst | Pt/H-mordenite | A | B | C |
|---|---|---|---|---|
| $C_5$ and lower | 51.0 | 1.0 | 0.0 | 10.7 |
| $C_6$ paraffins | 2.6 | 13.4 | 0.6 | 44.2 |
| $C_6$ unsaturates | 0.4 | 0.6 | 0.5 | 0.5 |
| Naphthenes | 0.1 | 0.0 | 0.2 | 0.0 |
| Aromatics | 43.1 | 8.4 | 5.3 | 7.0 |
| Total conversion | 97.2 | 23.3 | 6.5 | 62.4 |

The following Examples 4 to 6 illustrate the process of the invention in which ammonia is used to moderate the cracking reaction without affecting the dehydroisomerization of methylcyclopentane to benzene.

EXAMPLE 4

When the previously-employed Pt/H-mordenite catalyst is used at a temperature of 350° C., 36.5% of the MCP is hydrocracked and 34.4% goes to benzene and toluene (25.0 and 9.4% respectively); the total conversion of MCP being 80.6% as shown in Table 2 above.

After a slug of 2 ml of ammonia is passed over the catalyst (100 mg), also at 350° C., the activity pattern is completely changed. As a consequence of the ammonia treatment, the hydrocracking of MCP is reduced from 36.5 to 2.0% and the benzene yield is increased from 25.0 to 33.7% the toluene yield was not determined. The selectivity for aromatics increased from 42.8% to at least 66.1% and the selectivity for compounds having 6 or more carbon atoms was increased from 54.7 to 96.1%.

EXAMPLE 5

With a Pt/H-mordenite comprising 0.6% by weight of platinum and having a silica : alumina ratio of 11.4:1 the change of the activity pattern was followed as a function of the amount of ammonia taken up by the catalyst.

The results obtained are set out diagrammatically in FIG. 1 of the accompanying Drawings in which the molar percentages of MCP converted into benzene, benzene + toluene, and $C_5$ and lower compounds are plotted against the amount of ammonia adsorbed by the catalyst, expressed in mole of absorbed ammonia per gram of catalyst. Curve (A) shows the conversion of MCP into benzene; (B) shows the conversion of MCP into benzene + toluene; and (C) shows the conversion of MCP into $C_5$ and lower compounds. Study of these curves shows that the hydrocracking reaction — after an initial slight increase — is selectively suppressed proportionally to the amount of ammonia adsorbed by the catalyst. The conversion of MCP to aromatics is not poisoned at all; on the contrary, an increase conversion is observed. The toluene content of the aromatics fraction decreases particularly after so much ammonia is added that a further addition of ammonia is no longer completely adsorbed. In the Drawing, this is the case after about 425μ mole $NH_3$/g catalyst has been adsorbed.

EXAMPLE 6

The results obtained in a similar experiment to that described in Example 4 are set out below in Table 6. The hydrocracking was reduced from 32.6 to 3.8% upon addition of 2 ml of ammonia gas. The aromatics yield (benzene + toluene) increased from 34.4 to 51.9% and the selectivity for producing aromatics increased from 45.9 to 75.0% (Table 6, columns 1 and 2).

Then another pulse of MCP was passed over the catalyst to test whether any moderation effect was still detectable. The results given in column 3 (hydrocracking 5.5% aromatics 44.8% aromatics selectivity 68.3%) confirm that the effect of the ammonia treatment has some permanent character. This appears more clearly from the results obtained when subsequently hydrogen was passed over the catalyst for 24 hours at 350° C., followed by another pulse of MCP. The hydrocracking being 12.4%, the aromatics yield 42.9% and the aromatics selectivity 65.0% (column 4).

Thereafter the catalyst was heated at 400° C. for 1 hour and cooled down again at 350° C. As a result of the heat treatment 59.3 $\mu$ mole of $NH_3$/g catalyst were desorbed. The hydrocracking went up to 17.0%, which value is only half that of the non-moderated catalyst. The aromatics yield and the aromatics selectivity are 38.8 and 58.8% (column 5). The same procedure was repeated, except that the heat treatment was given at 450 and 500° C. The amounts of ammonia desorbed were 96.8 and 108.4 $\mu$ mole $NH_3$/g, respectively. The corresponding results are shown in columns 6 and 7, respectively. It is seen that even after the treatment at 500° C., the effect of the ammonia moderation had not entirely disappeared. MCP was less cracked and more MCP went to aromatics, then with the unmoderated catalyst.

the particular conditions, all three reactions are completely suppressed when more than 900$\mu$ mole of ammonia per g of catalyst are adsorbed. This amount corresponds to only a fraction of the total acidity of the sieve, which, as calculated from its alumina and sodium content, is as high as 2550 $\mu$ eq/g sieve.

More detailed analysis of the results shown in FIG. 2, taking into account the unfavorable thermodynamics for the conversion of MCP to cyclohexane (at 300° C. the MCP : cyclohexane molar equilibrium ratio is 4.0:1) indicates that the actual ratio of the two compounds leaving the reactor is close to the equilibrium ratio over the whole of the nearly horizontal portion of curve B. Therefore, the conclusion is that the ring isomerization is thermodynamically, and not kinetically controlled. Only when sufficient isomerization sites have been poisoned, do the kinetics become controlling, as reflected by a kink in curve B and by a departure of the actual MCP : cyclohexane ratio from the equilibrium ratio.

From this it would be expected that, in the absence of controlling thermodynamics, the dashed line would represent the actual relationship between the ring isomerization reaction and the ammonia adsorbtion.

Therefore, in contrast with what is suggested by FIG. 2, at a temperature of 300° C. ammonia does constitute a poison for the isomerization reaction. However upon increasing the temperature from 300 to 350° C., the results of Examples 4 to 6 show that ammonia ceases to be a nonselective poison for all reactions, but instead enhances the selectivity, favoring the isomerization reaction.

EXAMPLE 8

The conversion of n-hexane at 350° C. was investigated, using Pt/H-mordenite from which previously adsorbed ammonia was largely desorbed by heating the Table 6

|  | Unmoderated Catalyst | Catalyst Moderated with 1 Pulse of 2 ml NH$_3$ | | | | | |
| --- | --- | --- | --- | --- | --- | --- | --- |
|  |  | First MCP Pulse | Second MCP PUlse | After 24 h at 350° C. | After 1 h at 400° C. | After 1 h at 450° C. | After 1 h at 500° C. |
| Hydrocracking (formation of C$_5$ and lower) | 32.6% | 3.8% | 5.5% | 12.4% | 17.0% | 20.4% | 24.6% |
| C$_6$ paraffins | 7.3 | 12.6 | 10.8 | 9.1 | 8.4 | 7.9 | 8.5 |
| Naphthenes | 0.6 | 0.9 | 1.2 | 1.6 | 1.8 | 1.9 | 2.1 |
| Aromatics | 34.4 | 51.9 | 44.8 | 42.9 | 38.8 | 37.1 | 36.4 |
| Total conversion | 74.9 | 69.2 | 62.3 | 66.0 | 66.1 | 67.3 | 71.6 |
| C$_6$ selectivity | 56.5 | 94.5 | 91.2 | 81.2 | 74.3 | 69.7 | 65.6 |
| Aromatics selectivity | 45.9 | 75.0 | 68.3 | 65.0 | 58.8 | 55.1 | 50.9 |

EXAMPLE 7

The poisoning effect of ammonia was studied making use of a hydrogen mordenite catalyst with no catalytically active metal supported on it.

The catalyst was saturated with ammonia stepwise at 300° C., and used for the conversion of methylcyclopentane at 300° C. The results are set out in FIG. 2 of the accompanying Drawings in which the molar percentage of methylcyclopentane that is converted, is plotted against the amount of ammonia adsorbed by the catalyst, in $\mu$ mole/gram. The amounts of product produced by hydrocracking, ring isomerization and ring opening are shown, respectively, by curves A, B and C.

Curve B shows that ring isomerization (from methylcyclopentane to cyclohexane) is hardly affected in the initial stage of the poisoning (up to 500 $\mu$ mole $NH_3$/g catalyst). This in contrast to the hydrocracking and ring opening reactions (curves A and C), which are gradually poisoned over the entire range. It is seen that under catalyst at 500° C. (Run A), and using the same catalyst again exposed to an excess of ammonia at 350° C. (Run B).

The product breakdown is set out in Table 7.

Table 7

|  | Mole % Basis Charge | |
| --- | --- | --- |
| Run | A | B |
| Methane | 0.7 | 0.8 |
| Ethane | 2.7 | 2.7 |
| Propane | 27.4 | 8.8 |
| Isobutane | 5.6 | 1.7 |
| Butane | 4.0 | 3.6 |
| Isopentane | 4.0 | 2.1 |
| Pentane | 2.1 | 1.9 |
| 2,2-dimethylbutane | 5.7 | 4.4 |
| 2-methylpentane (including 2,3-dimethylbutane, if any, present) | 21.4 | 27.1 |
| 3-methylbutane | 11.8 | 15.5 |
| MCP | 0.3 | 0.6 |
| Benzene | 0.6 | 0.8 |

Table 7-continued

| Run | Mole % Basis Charge | |
|---|---|---|
| | A | B |
| n-hexane (unconverted) | | Remainder |
| | to 100 | 100 |

It will be seen that, in Run B, there is a sharp reduction in the formation of by-product propane, a lower conversion of n-hexane, and higher yields of 2-methylpentane and 3-methylpentane, obtained with the ammonia-treated catalyst.

A summary of the results (again in mole % basis charge) is given below in Table 8.

Table 8

| Run | A | B |
|---|---|---|
| Hydrocracking | 46.7 | 21.5 |
| Isomerization | 38.9 | 47.0 |
| Total Conversion | 86.4 | 69.9 |
| $C_6$-selectivity | 45.9 | 69.3 |

A sharp reduction of hydrocracking is the predominant factor.

We claim:

1. A process for the dehydroisomerization of alkylcyclopentane and hydrocarbon charge stocks containing alkylcyclopentane into aromatic hydrocarbons by contacting said alkylcyclopentane at an elevated temperature of at least 330° C. in the presence of hydrogen and a catalyst comprising a metal of Group VIII of the Periodic System supported on mordenite in hydrogen form treated with ammonia.

2. A process according to claim 1 wherein said Group VIII metal is platinum.

3. A process according to claim 1 wherein said catalyst comprises from about 0.01 to 5.0 weight percent platinum.

4. A process according to claim 1 wherein said catalyst comprises from about 0.1 to 1.0 weight percent platinum.

5. A process according to claim 1 wherein said catalyst additionally comprises a metal of Groups VI A or VII A.

6. A process according to claim 1 wherein said catalyst additionally comprises rhenium.

7. A process according to claim 1 wherein said alkylcyclopentane is methylcyclopentane.

8. A process according to claim 1 wherein said hydrocarbon charge stock is a naphtha fraction containing alkylcyclopentane.

9. A process according to claim 1 wherein said elevated temperature is in the range of from 350 to 500° C.

10. A process according to claim 1 wherein said elevated temperature is from 350 to 400° C.

11. A process according to claim 1 wherein said catalyst is treated with ammonia prior to contacting with said alkylcyclopentane.

12. A process according to claim 1 wherein said catalyst is contacted simultaneously with ammonia and said alkylcyclopentane.

13. A process according to claim 1 wherein said catalyst is contacted alternately with ammonia and with said alkylcyclopentane.

* * * * *